(12) United States Patent
Bhattacharyya et al.

(10) Patent No.: US 7,985,882 B1
(45) Date of Patent: Jul. 26, 2011

(54) COMPOSITIONS FOR REDUCTIVE AMINATIONS UTILIZING SUPPORTED TRICARBOXYBOROHYDRIDE REAGENTS AND METHODS OF USING THE SAME

(75) Inventors: Sukanta Bhattacharyya, Belmont, CA (US); Jeffrey W. Labadie, Sunnyvale, CA (US); Owen W. Gooding, Los Gatos, CA (US); Sunil Rana, San Carlos, CA (US)

(73) Assignee: Biotage AB, Uppsala (SE)

( * ) Notice: Subject to any disclaimer, the term of this patent is extended or adjusted under 35 U.S.C. 154(b) by 1207 days.

(21) Appl. No.: 10/226,637

(22) Filed: Aug. 23, 2002

(51) Int. Cl.
C07C 209/24 (2006.01)
(52) U.S. Cl. ............................ 564/472; 506/43; 544/141
(58) Field of Classification Search .................. None
See application file for complete search history.

(56) References Cited

U.S. PATENT DOCUMENTS

| | | | |
|---|---|---|---|
| 5,663,245 | A | 9/1997 | Kennedy et al. |
| 5,773,512 | A | 6/1998 | Chenera et al. |
| 5,859,277 | A | 1/1999 | Whitlock et al. |

FOREIGN PATENT DOCUMENTS

| | | |
|---|---|---|
| DE | 42 34 898 C1 | 4/1994 |
| FR | 2 536 752 | 11/1982 |
| FR | 2 616 152 | 6/1987 |
| WO | WO-97/44367 A1 | 11/1997 |
| WO | WO-98/05671 A1 | 2/1998 |
| WO | WO-98/17695 A1 | 4/1998 |

OTHER PUBLICATIONS

Kirschning, A. "Borohydride exchange resins (BER)—a group of versatile and powerful polymer-supported reductants" J. Prakt. Chem., 2000, 342, 508-511.*
Abdel-Magid et al. "Reductive Amination of Aldehydes and Ketones with Sodium Triacetoxyborohydride. Studies on Direct and Indirect Reductive Amination Procedures" J. Org. Chem. 1996, 61, 11, 3849-3862.*
Gribble et al. "Reactions of Sodium Borohydride in Acidic Media: V. Reduction and Alkylation of Oximes with Carboxylic Acids: A New Synthesis of N,N-Dialkylhydroxylamines," Synthesis, 1977, 12, 856-859.*
Gribble et al. "Reactions of Sodium Borohydride in Acidic Media. Selective Reduction of Aldehydes with Sodium Triacetoxyborohydride" J. Chem. Soc. Chem. Comm., 1975, 535-536.*
Labadi et al., "Polymer-supported borohydride, cyanoborohydride, and triacetoxyborohydride: Scope and selectivity in reduction and reductive amination" Abstracts of Papers, 222n ACS National Meeting, Chicago, IL, United States, Aug. 26-30, 2001.*
March, J.; Smith, M. B. Advanced Organic Chemistry Fifth Edition. New York: John Wiley and Sons, Inc. 2001, pp. 1197 and 1198.*
Abdel-Magid et al., "Reductive Amination of Aldehydes and Ketones with Sodium Triacetoxyborohydride. Studies on Direct and Indirect Reductive Amination Procedures", J. Org. Chem., vol. 61, pp. 3849-3862, 1996.

Battacharyya, "Titanium(IV) Isopropoxide and Sodium Borohydride: A Reagent of Choice for Reductive Amination", Tetrahedron Letters, vol. 35, No. 15, pp. 2401-2404, 1994.
Bhattacharyya et al., "Use of Zinc Borohydride in Reductive Amination: An Efficient and Mild Method for N-Methylation of Amines", J. Chem. Soc., Perkin Trans. 1, pp. 1-2, 1994.
Boehm et al., Development of a Novel Silyl Ether Linker for Solid-Phase Organic Synthesis, J. Org. Chem., vol. 61, pp. 6498-6499, 1996.
Booth et al., "Polymer-Supported Quenching Reagents for Parallel Purification", J. Am. Chem. Soc., vol. 119, pp. 4882-4886, 1997.
Borch et al., "The Cyanohydridoborate Anion as a Selective Reducing Agent", J. Am. Chem. Soc., vol. 93, No. 11, Jun. 2, 1971.
Brown et al., "Synthesis of Tertiary Amines Using a Polystyrene (REM) Resin", J. Am. Chem. Soc., vol. 119, pp. 3288-3295, 1997.
Chenera et al., "Protodetachable Arylsilane Polymer Linkages for Use in Solid Phase Organic Synthesis", J. Am. Chem. Soc., vol. 117, pp. 11999-12000, 1995.
Drewry et al., "Solid-Supported Reagents in Organic Synthesis", Medical Research Reviews, vol. 19, No. 2, pp. 97-148, Mar. 1999.
Emerson et al., "Secondary and Tertiary Amines from Nitro Compounds", J. Am. Chem. Soc. vol. 63, pp. 749-750, 1942.
Farrall et al., "Bormination and Lithiation: Two Important Steps in the Functionalization of Polystyrene Resins", J. Org. Chem., vol. 41, No. 24, pp. 3877-3882, 1976.
Flynn et al., "Chemical Library Purification Strategies Based on Principles of Complementary Molecular Reactivity and Molecular Recognition", J. Am. Chem. Soc., vol. 119, pp. 4874-4881, 1997.
Ghose et al., "A Knowledge-Based Approach in Designing Combinatorial or Medicinal Chemistry Libraries for Drug Discovery. 1. A Qualitative and Quantitative Characterization of Known Drug Databases", J. Comb. Chem., vol. 1, pp. 55-68, 1999.

(Continued)

*Primary Examiner* — Christopher M Gross
(74) *Attorney, Agent, or Firm* — Birch, Stewart, Kolasch & Birch, LLP.

(57) ABSTRACT

A modified solid-support for use as a supported reagent for use in reduction reactions, including reductive amination comprising a solid-support having an tetrasubstituted ammonium cation species ionically bonded to a borohydride anion species extending therefrom having the general formula:

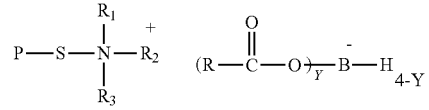

wherein
P is a solid-support, S is a spacer group selected from the group consisting of alkylene, {including $—(CH_2)_n—$}, alkyleneoxy {including $-O(CH_2)_n—$}, alkylenethio {including $—S(CH_2)_n—$} and alkylenecarboxy, {including $—O(O)C—(CH2)_n—$}, n=2-16. $R_1$, $R_2$, $R_3$ and R are each independently selected from the group consisting of alkyl, cycloalkyl, haloalkyl and aryl. Y equals 1, 2 or 3. H is hydrogen or deuterium.

14 Claims, 1 Drawing Sheet

OTHER PUBLICATIONS

Gibson et al., "Chemical Modification of Polymers. Borohydride Reducing Agents Derived from Anion Exchange Resins", J.C.S. Chem. Comm., vol. 1, p. 815, 1977.

Gribble et al., "Reactions of Sodium Borohydride in Acidic Media. Selective Reduction of Aldehydes with Sodium Triacetoxyborohydride", J.C.S. Chem. Comm., vol. 1, pp. 535-536, 1975.

Gribble et al., "Sodium Borohydride in Carboxylic Acid Media. A Review of the Synthetic Utility of Acyloxyborohydrides", Org. Prep. Proceed. Int., vol. 17, pp. 319-384, 1985.

Guyot et al., "Polymer Grafted on Porous Silica as Supports for Catalysts and Reagents", Makromol Chem.; Macromol. Symp., vol. 70/71, pp. 265-274, 1993.

Hodge et al., "Polymer-Supported Reagents in Organic Sythesis", Wiley & Sons Ltd., pp. 83-155, 1980.

Hu et al., "Novel Polymer-Supported Trialkylsilanes and Their Use in Solid-Phase Organic Synthesis", J. Org. Chem., vol. 63, pp. 4518-4521, 1998.

Hutchins et al., "Cyanoborohydride Supported on an Anion Exchange Resin as a Selective Reducing Agent", J.C.S. Chem. Comm., vol. 1, pp. 1088-1089, 1978.

Johnson et al., "N-Alkylation of Amides. A Novel Procedure", J. Org. Chem., vol. 27, pp. 2205, Jun. 1962.

Kaldor et al., "Use of Solid Supported Nucleophiles and Electrophiles for the Purification of Non-Peptide Small Molecule Libraries", Tetrahedron Letters, vol. 37, No. 40, pp. 7193-7196, 1996.

Ley et al., "Multi-Step Organic Synthesis Using Solid-Supported Reagents and Scavengers: A New Paradigm in Chemical Library Generation", J. Chem. Soc., Perkin Trans. 1, pp. 3815-4195, 2000.

Maxson et al., "Silicon-Containing Solid Support Linkers", Amer. Chem. Soc., 212th ACS Nat. Meeting, abstract No. 405, 1996.

Mitchell et al., "A New Synthetic Route to tert-Butyloxycarbonylaminoacyl-4-(oxymethyl)phenylacetamidomethyl-resin, an Improved Support for Solid-Phase Peptide Synthesis", J. Org. Chem., vol. 43, No. 14, pp. 2845-2852, 1978.

Muzafarov et al., "Degradable Hyperbranched Poly(bis(undecenyloxy)methylsilane)s", Amer. Chem. Soc., Macromolecules, vol. 28, No. 24, pp. 8444-8446, Nov. 1995.

Newlander et al., "Simple Silyl Linder for the Solid Phase Organic Synthesis of Aryl-Containing Molecules", J. Org. Chem., vol. 62, pp. 6726-6732, 1997.

Patchomik et al., "The Use of Polymeric Reagents in Organic Synthesis", Pure Appl. Chem., vol. 43, pp. 503-526, 1975.

Pelter et al., "Reductive Aminations of Ketones and Aldehydes Using Borane-Pyridine", J. Chem. Soc., Perkin Trans., No. 1, pp. 717-720, Jan. 1984.

Plunkett et al., "A Silicon-Based Linker for Traceless Solid-Phase Synthesis", J. Org. Chem., vol. 60, pp. 6006-6007, 1995.

Scott et al., "The Use of Resin Coated Glass Beads in the Form of a Packed Bed for the Solid Phase Sythesis of Peptides", J. Chrom. Science, vol. 9, pp. 577-591, 1971.

Shuttleworth et al., "Functionalised Polymers: Recent Developments and New Applications in Synthetic Organic Chemistry", J. Synthetic Org. Chem., No. 7, pp. 1217-1239, Jul. 1997.

Stranix et al., "Functional Polymers from (Vinyl)polystyrene. Recyclable Polymer-Supported Organosilicon Protecting Groups for Solid-Phase Synthesis", J. Org. Chem., vol. 62, pp. 6183-6186, 1997.

Thompson et al., "Synthesis and Applications of Small Molecule Libraries", Chem. Rev., vol. 96, pp. 555-600, 1996.

Woolard et al., "A Silicon Linker for Direct Loading of Aromatic Compounds to Supports. Traceless Sythesis of Pyridine-Based Tricyclics", J. Org. Chem., vol. 62, pp. 6102-6103, 1997.

* cited by examiner

US 7,985,882 B1

COMPOSITIONS FOR REDUCTIVE AMINATIONS UTILIZING SUPPORTED TRICARBOXYBOROHYDRIDE REAGENTS AND METHODS OF USING THE SAME

FIELD OF THE INVENTION

The present invention relates to a modified solid-supported reagent for use in organic synthesis. More particularly, the invention relates to modified solid-supported reagents having tricarboxyborohydrides groups extending therefrom.

BACKGROUND OF THE INVENTION

The selective reduction of functional groups is a common need in organic synthesis. Borohydrides and derivatives are widely used in synthetic organic chemistry in the reduction of a variety of functional groups (e.g., carbonyls, imines, azides, nitro and disulfides). Tricarboxyborohydrides are useful in reductive amination reactions in which a carbonyl compound and an amine are condensed in the presence of a tricarboxyborohydride, e.g., sodium triacetoxyborohydride, to afford a higher order amine derivative. [See, Gribble et al, J. Chem. Soc., Chem. Comm. 1975, 535 and Abdel-Majid et al, J. Org. Chem. 1996, 61, 3849]. Reductive amination is a widely employed reaction in discovery research, i.e., in drug discovery. The aliphatic tertiary amines alone constitute a quarter of drugs currently in the market [Morphy et al, J. Am. Chem. Soc. 1997, 119, 3288] and may be synthesized by reductive amination reaction. Amines and their carboxamide derivatives are some of the most abundant functional groups found in drugs and constitute around 75% of the drug database [Ghose, Viswanadhan, Wendoloski, J. Combi. Chem. 1999, 1, 55].

The reaction conditions for reductive aminations primarily use catalytic hydrogenation and hydride-based reducing agents. The catalytic hydrogenations mostly employ Pd, Pt or Ni catalysts. [See, Emerson, Uraneck, J. Am. Chem. Soc. 1941, 63, 749; Johnson; Crosby, J. Org. Chem. 1962, 27, 2205]. However, reduction of C—C multiple bonds and other reducible groups is a major limitation. Some of the hydride based reducing agents used for reductive amination reactions mainly include, sodium cyanoborohydride [Borch, Bernstein, J. Am. Chem. Soc, 1971, 93, 2897], borane-pyridine [Pelter, Rosser, Mills, J. Chem. Soc. Perkin Trans 1 1984, 717], NaBH$_4$/Ti(O$^i$Pr)$_4$ [Bhattacharyya, Tetrahedron Lett. 1994, 35, 2401], Zn(BH$_4$)$_2$/ZnCl$_2$ [Bhattacharyya et al, J. Chem. Soc. Perkin Trans 1, 1994, 1] and sodium triacetoxyborohydride [Gribble, Nutaitis, Org. Prep. Proceed. Int. 1985, 17, 319; Abdel-Majid et al, J. Org. Chem. 1996, 61, 3849].

The use of polymer-supported reagents provides an attractive, practical approach to organic synthesis. A primary benefit of using these modified reagents is their ability to facilitate product isolation. By using polymer-supported reagents and scavengers, the reaction by-products and excess starting material(s) may be selectively removed from the crude reaction mixture by simple filtration of resin instead of other separation techniques such as liquid-liquid extraction and/or flash chromatography. Moreover polymer-supported reagents can provide unique advantages relative to their solution counterparts including selectivity, immobilization of toxic reagents, isolable reactive intermediates and the ability to simultaneously use relatively incompatible reagents, e.g., an acid and base, or perform multiple transformations in a single flask. The development and use of polymer-supported reagents began in the 1970's [Patchornik et al, Pure Appl. Chem. 1975 43, 503; *Polymer-supported Reagents in Organic Synthesis* P. Hodge and D. C. Sherrington, Ed.: Wiley, 1980] and has seen a revival in about the last five years based on reports form several pharmaceutical research laboratories demonstrating their benefit for parallel synthesis. [Kaldor et al, Tetrahedron Lett. 1996, 37, 7193; Booth et al, J. Am. Chem. Soc. 1997, 119, 4882; Flynn, D. L. J. Am. Chem. Soc. 1997, 119, 4874]. There have been several comprehensive reviews recently that describe the current state of the field. [Ley et al, J. Chem. Soc. Perkin Trans 1, 2000, 3815; Drewery et. al, Med. Res. Rev. 1999, 19, 97; Shuttleworth et al Synthesis, 1997, 1217].

For example, polymer-supported borohydrides have been developed to facilitate reductive amination reactions. Borohydride (BH$_4^-$) has been reported based on anion exchange resin with the general formula P—NR$_3^+$BH$_4^-$ [Gibson et. al., J. Chem. Soc. Chem. Comm. 1977, 815]. This was shown to be relatively effective in the reduction of aldehydes, ketones, alpha-beta unsaturated alcohols, azides, and other reducible organic moieties. Polymer-supported cyanoborohydrides [(CN)BH$_3^-$] have been also reported based on anion exchange resin with the general formula P—NR$_3^+$ (CN)BH$_3^-$ [Hutchins, et. al., J. Chem. Soc., Chem. Comm. 1978 1088]. This was shown effective in the reduction of aldehydes, ketones, alpha-beta unsaturated alcohols, azides, and other reducible organic moieties. However sodium cyanoborohydrides has been known to produce relatively toxic cyanide residues. These and other known supported borohydrides have been observed to also provide relatively modest yields and limited chemoselectivity. There is a need for an improved solid-supported borohydride reagent.

SUMMARY OF THE INVENTION

The present invention provides solid-supported triacetoxyborohydride ((AcO)$_3$BH—) reagents. These reagents can basically mimic the action of the small molecule sodium triacetoxyborohydride as is known and taught by Abdel-Majid, et al. [J. Org. Chem. 1996, 61, 3849-3862]. The supported versions of this small molecule herein offer a number of important advantages over other borohydrides and cyanoborohydrides available today, particularly those selected for applications such as reductive amination reactions of aldehydes and ketones. [See, Abdel-Majid, et al, J. Org. Chem. 1996, 61, 3849-3862].

The solid-supported versions of triacetoxyborohydride provided herein combine the benefits of using polymer-supported reagents with this versatile and increasingly popular molecule. The invention leverages the benefits of using a solid-support medium with triacetoxyborohydride as a reagent. The supported reagents herein are relatively milder and more chemoselective than either sodium borohydride or sodium cyanoborohydride products, and may often obtain higher yields in selected reactions. The solid-supported triacetoxyborohydride reagents provided also do not have the potential to release toxic cyanide residues that could contaminate a desired product as would often occur with sodium cyanoborohydride. Moreover sodium triacetoxyborohydride has largely supplanted the use of both sodium borohydride or sodium cyanoborohydride today for the commonly employed reductive amination reactions. The supported versions of triacetoxyborohydride herein offer further advantages including the ease of dispensing the moisture sensitive reagent, and the facilitation of work-up and isolation of the products, which is a desirable attribute of supported reagents in organic synthesis.

It is therefore an object of the invention to provide modified solid-supports for use as a supported reagent in reduction reactions, including reductive amination. A solid-supported reagent may comprise: a solid-support having a tetra-substituted ammonium species ionically linked to a borohydride anion species extending therefrom having the general formula:

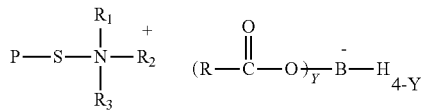

wherein

P is a solid-support. S is a spacer group selected from the group consisting of alkylene, {including —$(CH_2)_n$—}, alkyleneoxy {including -$O(CH_2)_n$—}, alkylenethio {including —$S(CH_2)_n$—} and alkylenecarboxy, {including —$O(O)C$—$(CH2)_n$—} wherein n=1-20. $R_1$, $R_2$, $R_3$ and R are each independently selected from the group consisting of alkyl, cycloalkyl, haloalkyl and aryl. Y=1, 2 or 3. H is hydrogen or deuterium.

The above materials and other embodiments of the invention have the advantage of addressing many of the difficulties in using sodium triacetoxyborohydride and sodium cyanoborohydride in solution where reactions must be quenched and the spent reagents removed by liquid-liquid extraction, chromatography, or other means other than simple filtration. Moreover there are other advantages relative to polymer-supported cyanoborohydride in that toxic cyanide residues are not generated. The versatility of using supported triacetoxyborohydride as provided herein significantly adds to its commercial value.

Another aspect of the invention provides methods for synthesizing supported carboxyborohydride compounds, as well as methods for using them in reductions, including reductive amination. For example, methods are provided herein for synthesizing a modified solid-support for use as a solid-supported reagent.

In one embodiment, the method comprises the steps of:

selecting a solid-support having an tetraalkyl ammonium group ionically linked to borohydride; and reacting the supported reagent with Y equivalents of carboxylic acid $RCO_2H$ wherein R is selected from the group consisting of alkyl, cycloalkyl, haloalkyl and aryl. Accordingly, a polymer-supported carboxyborohydride may be formed having the general formula:

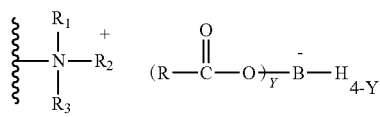

wherein $R_1$, $R_2$, $R_3$ and R are each independently selected from the group consisting of alkyl, haloalkyl, cycloalkyl, and aryl. Y equals 1, 2 or 3. H is hydrogen or deuterium. Additionally, other supported reagents synthesized herein may have the general formula:

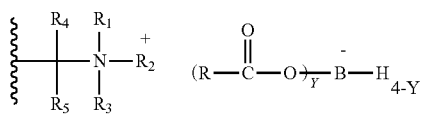

wherein $R_4$ and $R_5$ are each independently selected from the group consisting of hydrogen, alkyl, cycloalkyl, and aryl. $R_1$, $R_2$, $R_3$ and R are each independently selected from the group consisting of alkyl, haloalkyl, cycloalkyl, and aryl. Y equals 1, 2 or 3. H is hydrogen or deuterium.

Other embodiments of the invention may be also described with the following general formula:

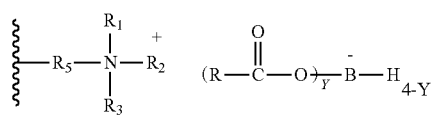

wherein $R_5$ is selected from the group consisting of alkylene {including —$(CH2)_n$—}, alkyleneoxy {including -$O(CH_2)_n$—}, alkylenethio {including —$S(CH_2)_n$—} and alkylenecarboxy {including —$O(O)C$—$(CH2)_n$—} wherein n=1-20, and $R_1$, $R_2$, $R_3$ and R are each independently selected from the group consisting of alkyl, cycloalkyl, haloalkyl and aryl. Y equals 1, 2 or 3. H is hydrogen or deuterium.

Additional embodiments of the invention may be formed using various ion-exchange methods of synthesis. For example, a selected method of forming supported reagents herein may comprise the steps of:

selecting a solid-support having an tetraalkyl ammonium group ionically linked to a halide, nitrate, or other group suitable for anion exchange; and reacting the supported reagent with a solution containing an excess of:

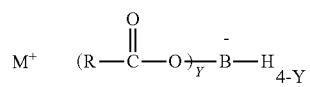

where M is lithium, sodium, potassium, tetraalkylammonium, benzyltrialkylammonium, or tetraphenylammonium, wherein R is selected from the group consisting of alkyl, cycloalkyl, haloalkyl and aryl. Accordingly, a polymer-supported carboxyborohydride may be formed having the general formula:

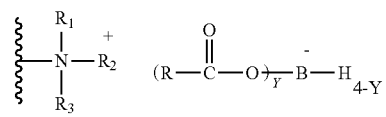

wherein $R_1$, $R_2$, $R_3$ and R are each independently selected from the group consisting of alkyl, haloalkyl, cycloalkyl, and aryl. Y equals 1, 2 or 3. H is hydrogen or deuterium. Additionally, other supported reagents synthesized herein may have the general formula:

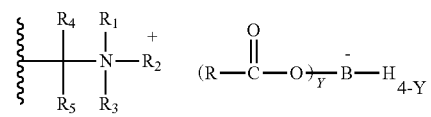

wherein $R_4$ and $R_5$ are each independently selected from the group consisting of hydrogen, alkyl, cycloalkyl, and aryl. $R_1$, $R_2$, $R_3$ and R are each independently selected from the group consisting of alkyl, haloalkyl, cycloalkyl, and aryl. Y equals 1, 2 or 3. H is hydrogen or deuterium.

Other embodiments of the invention may be also described with the following general formula:

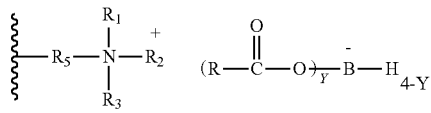

wherein $R_5$ is selected from the group consisting of alkylene {including —(CH2)$_n$—}, alkyleneoxy {including -O(CH$_2$)$_n$—}, alkylenethio {including —S(CH$_2$)$_n$—} and alkylenecarboxy {including —O(O)C—(CH2)$_n$—} wherein n=1-20, and $R_1$, $R_2$, $R_3$ and R are each independently selected from the group consisting of alkyl, cycloalkyl, haloalkyl and aryl. Y equals 1, 2 or 3. H is hydrogen or deuterium.

Methods are also provided herein for using solid-supported tricarboxyborohydrides in performing reductions, including reductive amination reactions. These and other objects of the invention will become apparent upon further consideration of the specification and drawings. While the following description may contain many specific details describing particular embodiments of the invention, this should not be construed as limitations to the scope of the invention, but rather as an exemplification of preferable embodiments. For each aspect of the invention, many variations are possible as suggested herein that are known to those of ordinary skill in the art.

DETAILED DESCRIPTION OF THE INVENTION

Figure 1:
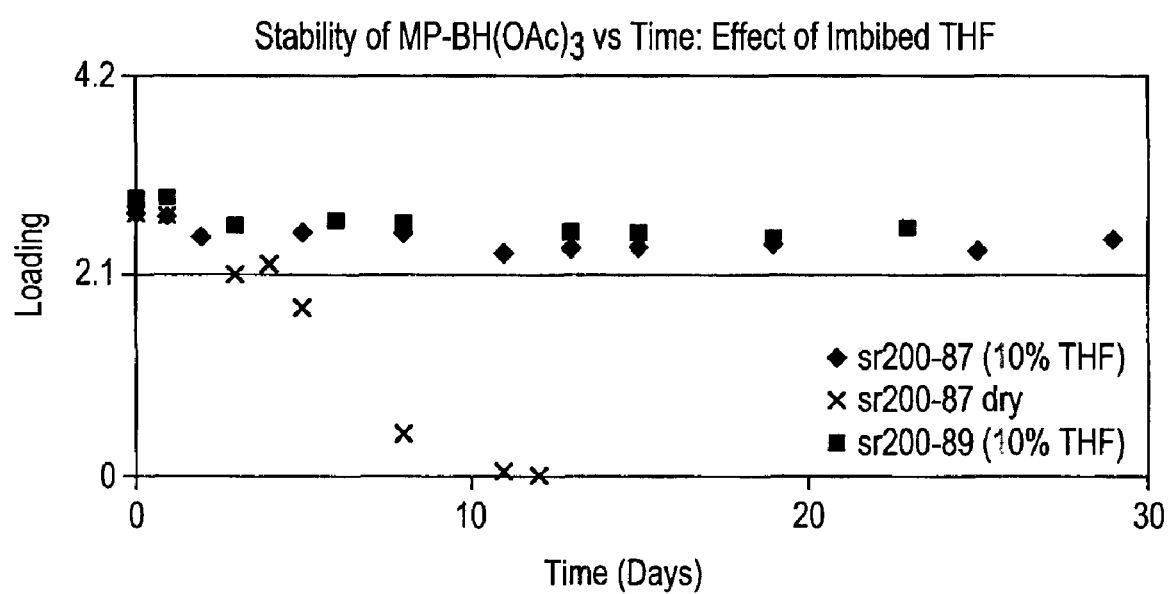
FIG. 1 shows the effect of imbibed THF on the stability of MP-BH(OAc)$_3$ over time.

Unless otherwise defined, all technical and scientific terms employed herein have their conventional meaning in the art. As used herein, the following terms have the meaning ascribed to them.

The terms "carbonyl compound," "carbonyl," and the like refer to compounds containing the carbonyl functional group, C=O, which is present in aldehydes and ketones.

The terms "reductive amination" and "reductive alkylation" refer broadly to the reactions of aldehydes or ketones (i.e., carbonyl compounds) with ammonia, primary amines, or secondary amines in the presence of reducing agents to yield primary, secondary, or tertiary amines, respectively. Carbonyl compounds are reductively aminated, while amines are reductively alkylated. There are two general types of reductive amination reactions, indirect (or stepwise) and direct. Direct reactions do not entail prior formation of the intermediate imine when the carbonyl compound and the amine are combined with an appropriate reducing agent. Conversely, indirect reactions entail the formation of the intermediate imine in a distinct step prior to the reduction [See, A. F. Abdel-Magid et al., J. Org. Chem. 61:3849-3862 (1996)]. The methods of the present invention may be employed with either direct or indirect reactions direct reactions.

The term "reducing agent" refers broadly to a compound (or a combination of compounds) which furnishes electrons to another. The term "hydride reducing agent" refers broadly to those reducing agents that comprise a hydrogen which assumes a negative charge (e.g., sodium borohydride and lithium aluminum hydride).

The term "solid-supports" refers to solid particles of any size and shape that are substantially insoluble in water and organic solvents at the temperatures and other conditions typically employed in solid phase synthesis reactions.

The term "solid-supported reagents" refers to solid-supports with functionality appended, either ionically or covalently, that can effect synthetic organic transformations The term "substantially insoluble" means that less than 20 percent of 1 g of the specified solid-support will solubilize in 1000 g of the specified solvent at 40° C. and at atmospheric pressure.

Furthermore, as used in this specification, the terms alkyl, cycloalkyl, and aryl refer to substituents having a straight chained or branched alkyl, a cycloalkyl or cyclic aromatic carbon backbone which may be optionally substituted with substituents having heteroatoms. The terms imines refer to any class of compounds containing a carbon atom double bonded to a nitrogen atom, C=N. The terms amines refer to any of a class of compounds derived from ammonia by replacement of one or more hydrogen atoms with organic groups.

Selection of Solid-Supports

Solid-supports (P) used in the present invention include particles conventionally employed as polymer reagents or polymer-supported reagents for organic synthesis. Solid-supports are typically functionalized with one or more functional groups. That is, the supports have one or more functional groups usually covalently linked thereto. The functional groups may be incorporated into the matrix that forms the particle, such as the polymer matrix, or may be covalently attached to the surface of the support. The functional groups can also be ionic in nature and provide an ionic site for bonding a counter-ion that can act as a reagent. This reagent can effect chemical transformations while staying bonded to the resin. Several types of solid phase particles having covalently bonded ionic functional groups and counter-ionic reagents have been described in the chemical and biochemical literature [See, *Polymer-supported Reagents in Organic Synthesis* P. Hodge and D. C. Sherrington, Ed.: Wiley, 1980 and Ley et al J. Chem. Soc. Perkin Trans 1, 2000, 3815].

The compositions of the present invention may include any of the many different known types of solid-supports, and is not limited by the nature of the functional group(s) linked to the particles. The solid phase support is however substantially insoluble in aqueous and organic solvents, and is substantially inert to the reaction conditions needed to employ the solid-support in chemical synthesis. The solid-supports that are currently available typically fall into one of four types or categories: (1) organic polymer resins; (2) silica based; (3) composites; and (4) surface-grafted objects. It shall be understood that the invention is not limited to a selection from to these four types of solid-supports which are described further below.

One type of solid phase support includes organic polymer resins which are commonly used for the synthesis of polypeptides, oligopeptides, oligonucleotides, and organic small molecules. These solid-supports comprise polymerized resins having functional groups attached thereto (i.e., "functionalized resins"). One example of a functionalized resin is hydrophobic polymerized styrene crosslinked with divinyl benzene (typically at about 0.5 to 20 weight percent). The polymerized resin is typically provided in the form of a spherical bead, which is further reacted to provide a known quantity of substituted benzyl moieties attached to the resin. A common resin is substituted with benzyl moieties, e.g., benzyl halides, which can be converted to tetralklyammonium halides by reaction with tertiary amine (anion exchanger). The halide anion can subsequently be ion exchanged with other reactive anions to afford polymer-supported reagents. These reagents can undergo further reaction at the anionic center to form new polymer-supported reagents. The reactive substituted benzyl moieties are typically added to the particle after the resin bead has been prepared. These supports are generally characterized as crosslinked poly-(styrene-co-divinylbenzene) resins that include a known quantity of disubstituted benzene crosslinks. Polymerized, crosslinked styrene-divinylbenzene resins containing chlorobenzyl moieties are sometimes referred to in the art as "chloromethyl styrene resins," while resins containing aminobenzyl moieties are sometimes referred to as "amino-styrene" or "aminomethyl-styrene resins." Chloromethyl styrene resins are available from a number of vendors, including Novabiochem (San Diego, Calif.), Advanced Chemtech (Louisville, Ky.), and Argonaut Technologies (Foster City, Calif.). These materials typically contain from 0.1 to 4 milliequivalents of chlorine per gram of particle. Resinous particles having aminobenzyl moieties may be also prepared from polymerized styrene cross-linked with divinyl benzene by reaction with N-(hydroxymethyl)phthalimide under Friedel-Crafts conditions followed by hydrazinolysis of the phthalimide group as described by A. R. Mitchell, S. B. H. Kent, M. Engelhard, R. B. Merrifield [J. Org Chem, 1978, 43, 2845-2852]. Particles containing aminobenzyl moieties are available from a number of vendors, including Novabiochem (San Diego, Calif.), Advanced Chemtech (Louisville, Ky.), and Argonaut Technologies (Foster City, Calif.). Typically the particles contain from about 0.1 to about 4 millimoles of aminobenzyl moiety per gram of particles.

Other functionalized polystyrenes that may be employed in the compositions of the present invention include but are not limited to polymerized polystyrene having carboxyl functional groups (i.e., carboxypolystyrene), polymerized polystyrene having hydroxymethyl functional groups (i.e., hydroxymethyl polystyrene), polymerized polystyrene having formyl functional groups (i.e., formyl polystyrene), polymerized polystyrene having sulfonyl functional groups (i.e., sulfonyl polystyrene), and polystyrene having bromomethyl functional groups (i.e., bromomethyl polystyrene). In addition, a group of grafted polystyrene resin solid-supports which may be employed in the compositions of the present invention include the ARGOGEL™ resins, which are commercially available from Argonaut Technologies (Foster City, Calif.) and the TENTAGEL™ resins, which are commercially available from Rapp Polymere (Tubingen, Federal Republic of Germany). Generally these resins are poly(ethylene oxide)-grafted polystyrene resin particles having functional groups which include alcohol group, alkyl amine groups, alkyl halide groups, alkyl thiol groups, or combinations thereof.

A second type of solid-support includes silica-containing particles such as porous glass beads and silica gel. Examples of these supports are described in A. Guyot, A. Revillon, E. Carlier, D. Leroux, C. Le Deore [Makromol. Chem. Macromol Symp., 1993, 70/71, 265-74].

A third type of solid-support includes composites of a resin and another material, both of which are substantially inert to the organic synthesis conditions. The other composite material may be a resin as well. One representative example of a composite material is reported in Scott et al. [J Chrom. Sci., 9, 577-591 (1971)]. Essentially this composite support includes glass particles coated with a hydrophobic, polymerized, crosslinked styrene containing a reactive chloromethyl group, and is commercially available from Northgate Laboratories (Hamden, Conn.).

A fourth type of solid-support which may be employed in the compositions of the present invention includes grafted polyethylene, polypropylene, polytetrafluoroethylene supports. These supports are often surface-grafted objects which are larger than resin beads, and include SYNPHASE™ Crowns (Chiron Technologies, Melbourne, Australia) and Irori MICROTUBES™ (Irori, La Jolla, Calif.). Generally these supports are comprised of polystyrene, polyacrylamide or polyacrylic acid grafts onto polystyrene or polypropylene cores, which have functional groups along the backbone, including amine, alcohol and other linkers.

Selection of Solvents

The solid-supports selected for the compositions and methods of the present invention are substantially insoluble in both organic and aqueous solvents. Several organic solvents which may be used in accordance with the invention are described below. It shall be understood however that the invention is not limited to this selection.

Generally less than 20 percent of 1 g of the selected support will solubilize in 1000 g of an aqueous or organic solvent at 40° C. and atmospheric pressure. More typically, less than 15 percent of 1 g of the support will solubilize in 1000 g of aqueous or organic solvent at 40° C. and atmospheric pressure. Preferably less than 10 percent of 1 g of the support will solubilize in 1000 g of aqueous or organic solvent at 40° C. and atmospheric pressure.

An important aspect of the present invention is that the solid-support remain substantially insoluble in the organic solvents with which it will be used. Organic solvents suitable for the present invention include but are not limited to those listed in the table below.

Examples of Organic Solvents for Use with Solid-Supports

Halocarbons dichloromethane, chloroform, trichloroethylene, tetrachloroethylene, [1,1,1]-trichloroethane, trichlorotrifluorethane, carbon tetrachloride), hydrocarbons (pentane, hexane, heptane, octane)

Aromatic Hydrocarbons benzene, toluene, xylene, m-cresol, chlorobenzene, trifluoromethyl benzene), amides (dimethyl formamide, dimethyl acetamide, N-methylpyrrolidinone), sulfoxides/sulfones (dimethyl sulfoxides, dimethyl sulfone, sulfolane)

Nitriles acetonitrile, ethyl nitrile

Ethers

Tetrahydrofuran, diethyl ether, [1,4]-dioxane

Organic Acids acetic acid, formic acid

Amines pyridine, triethanolamine

Esters butyl acetate, ethyl acetate, trimethyl phosphate

Nitro Compounds nitromethane, nitrobenzene

Preferable solvents include but are not limited to the following: tetrahydrofuran, pentane, hexane, heptane, benzene, toluene, xylene, m-cresol, dimethylformamide, dimethylacetamide, N-methylpyrrolidinone, dimethylsulfoxide, acetonitrile, dichloromethane, dichloroethane, chloroform, and trichloroethylene. Most preferably, the organic solvent used herein is selected from the group consisting of tetrahydrofuran, toluene, dimethyl formamide, N-methylpyrrolidinone, dimethyl sulfoxide, acetonitrile, and dichloromethane.

Selection of Spacer Group

The spacer group (S) provides the connection between the backbone of the solid-support and the reactive functional group. One of the principal functions of the spacer is to tether the reactive functional group away from the rigid backbone of the solid-support, thereby minimizing unintended effects on the chemical reactivity of the functional group. The spacer group may consist of a chain of atoms between 1 to 20 atoms or more in total. In some instances, it is desirable for no spacer group to be employed. When employed however the spacer group typically consists of an alkyl, branched alkyl, cycloalkyl or aryl grouping of atoms. This grouping may further contain branching and/or may contain heteroatoms. The spacer group may also consist of a combination of an alkyl, cycloalkyl, and aryl group.

In one embodiment of the invention, spacer groups may be employed which include linear alkyl chains containing between 1 and 20 atoms. These alkyl chains may optionally include heteroatoms (e.g., oxygen, sulfur, nitrogen) in its backbone. A wide variety of substituents may also be attached to the backbone.

Processes for Making and Using Supported Reagents Provided by the Present Invention The following examples serve to illustrate certain preferred embodiments and aspects of the present invention and are not to be construed as limiting the scope thereof.

Example 1

Synthesis of Tetraalkylammonium Triacetoxyborohydride Resin

Scheme 1: Synthesis of bound triacetoxyborohydride

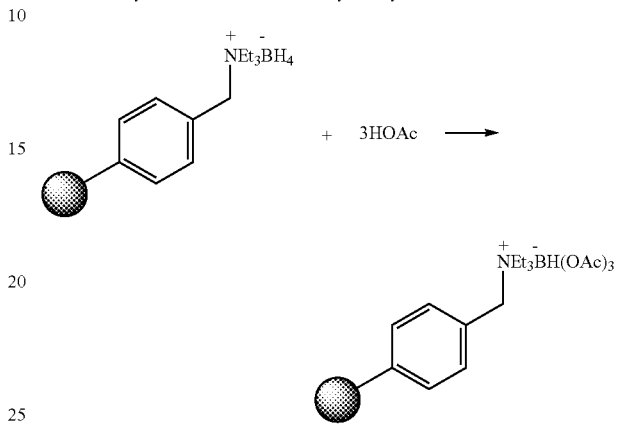

A dry 3 L, 4-necked reaction flask was placed into a large plastic reservoir for cooling. The flask was fitted with a mechanical stirring paddle, a thermocouple, an addition funnel, a nitrogen inlet and an oil bubbler to monitor out-gassing. The glassware was dried by warming to −50° C. with nitrogen flush, then allowed to cool to room temperature under nitrogen. The reactor was charged with 200 g MP-BH$_4$ resin (Argonaut Technologies, lot # 01794, 3.0 mmol/g), and filled with nitrogen. Anhydrous THF (600 mL) was added to the flask, and the suspension allowed to stir at 60 rpm. The suspension was cooled to −10° C. with ice-salt mixture under a flow of nitrogen. A solution of glacial acetic acid (112 g, 1.86 mol) in THF (400 mL) was prepared and transferred to the addition funnel. The nitrogen inlet was closed, and the acetic acid solution was added to the stirring suspension at a rate of 4 mL/minute. The temperature and rate of gas evolution were monitored closely during the addition. Gas evolution was fast at the beginning and slowed over time. When the temperature rose above 2° C., addition was stopped temporarily, while adding more ice and salt to the bath. Addition of the acetic acid solution was complete in about 2 hours.

The reaction mixture was agitated overnight by which time it had warmed up to room temperature. The reaction was then cooled again to approx +5° C. to −5° C. with a nitrogen flow and warmed up to room temperature again. The solvent was then removed through a filter tube, and the resin washed with 2×THF (1000 mL). The system was flushed with a strong stream of nitrogen during all washing processes. After the final THF wash, the beads were dried by passing a stream of nitrogen by inserting a Teflon tube into the resin beads. The beads were turned with occasional mechanical stirring in the reactor for at least 10 minutes until the point at which the batch became free-flowing without any clumps of resin. This process took about 15 minutes. The resin was transferred to a drying bottle and blown with nitrogen with vigorous mixing until the mass reduced to theoretical plus 10%. The beads should not be allowed to over-dry as that could destroy the resin. The mass of the bottle was checked periodically. When obtaining the mass, the bottle was closed so that the cold beads could not come into contact with air. The beads were then tested for loading. It shall be understood that the tetraalkylammonium triacetoxyborohydride resin obtained shall be referred to herein as MP-Triacetoxyborohydride.

Capacity Determination:

The resin sample was dried by blowing nitrogen for 2-3 minutes until it becomes relatively free-flowing. About 300 mg of the sample was weighed accurately in a 2-necked (B14 joint) 50 ml RB flask, having already placed a magnetic bar inside the flask. 20 ml of 1 M HCl solution was then filled in a 50 ml addition funnel with B14 joint, the bottom end of the addition tube should remain dry. The flask was connected via an outlet tube to a reservoir filled with water for collection of hydrogen gas. The HCl solution was the added dropwise with stirring and the generated hydrogen gas was collected, the reaction was allowed to proceed for 20 minutes until no more gas is generated. The volume of hydrogen gas collected was used to calculate the capacity of the resin. Triacetoxyborohydride was observed to release one equiv of hydrogen gas on hydrolysis.

Scheme 2: Capacity Determination of Bound Triacetoxyborohydride

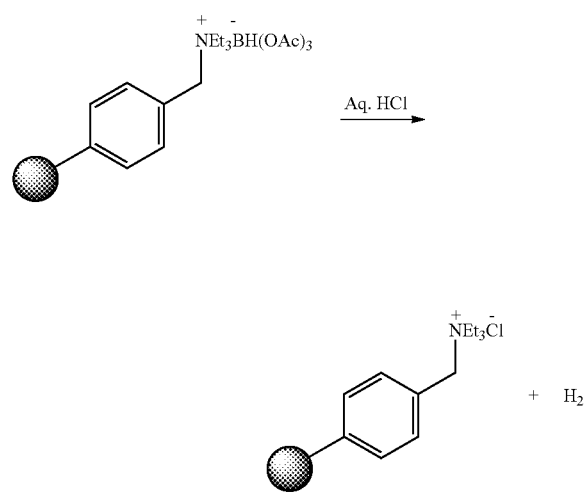

Examples 2

Synthesis of Secondary Amines by Reductive Amination using Tetraalkylammonium Triacetoxyborohydride Resin Scheme 3: Reductive Amination using Primary Amines: Synthesis of Secondary Amines

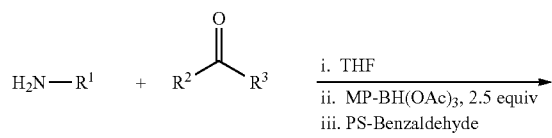

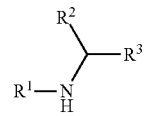

$R^1$ = Alkyl, Aryl

Representative Procedure for Synthesis of Secondary Amines

Entry 3, Table 1

A THF solution (0.50 M) of N-(3-aminopropyl)morpholine (1.2 mL, 0.60 mmol) was added to a THF solution (0.50 M) of 1,4-cyclohexanedione mono-ethylene ketal (1.0 mL, 0.50 mmol). MP-Triacetoxyborohydride (2.0 mmol/g, 0.625 g, 1.25 mmol) was then added and the mixture was agitated for 16 h at room temperature. When the reaction was complete, PS-Benzaldehyde (0.42 g, 0.5 mmol) and THF (2 mL) were added and the mixture was further agitated for 6 h. The solution was filtered and the resin was washed with THF (2×4 mL). The combined solution was concentrated to afford the product secondary amine as the acetate salt in 77% yield and 100% purity. The secondary amine was characterized by gas chromatography and $^1$H NMR.

Discussion of Example

The starting primary amine was used in 20% excess in order to control selectivity towards monoalkylation. Reductive amination reactions proceeded overnight at room temperature in THF under neutral reaction conditions. After the reaction was complete, PS-Benzaldehyde (Argonaut Technologies) was added to the reaction mixture, selectively scavenging excess primary amine. The product secondary amine may be isolated as the acetate salt by filtration of the resin and evaporation of the solvent. The free amine may be obtained by neutralization of the acetate salt with MP-Carbonate (Argonaut Technologies) or by "catch and release" purification with MP-TsOH or SCX columns (Argonaut Technologies).

The results for the reductive amination using a set of primary amines are summarized below in Table 1. In most of the cases the products were isolated in excellent purity. Reaction of cyclohexanecarboxaldehyde afforded 16 and 4% overalkylated tertiary amine product with N-(3-aminopropyl)morpholine and 2-(aminomethyl)pyridine, respectively (entries 1 and 2, Table 1). Acid sensitive functional groups were tolerated, as exemplified by successful reductive amination of 1,4-cyclohexanedione mono-ethylene ketal with N-(3-aminopropyl)morpholine and 2-aminomethylpyridine (entries 3 and 4, Table 1). Acetophenone underwent reductive amination in low to moderate yields, consistent with sodium triacetoxyborohydride (entries 5 and 6, Table 1).

TABLE 1

Synthesis of Secondary Amines by Reductive Amination using MP-Triacetoxyborohydride

| Entry | Starting Amine | Carbonyl Compound | Product Amine | % Yield (isolated) | % Purity |
|---|---|---|---|---|---|
| 1 | | | | 77 | 84[a] |
| 2 | | | | 90 | 96[a] |
| 3 | | | | 77 | 100 |
| 4 | | | | 91 | 100 |
| 5 | | | | 69 | 98 |
| 6 | | | | 76 | 27 | a) Dialkylated product present as the major impurity.

Examples 3

Synthesis of Tertiary Amines by Reductive Amination Using MP-Triacetoxyborohydride Resin Scheme 4: Reductive Amination using Secondary Amines: Synthesis of Tertiary Amines

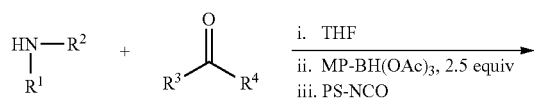

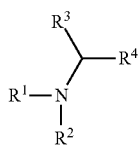

Representative Procedure for Synthesis of Tertiary Amines

Entry 1, Table 2

A THF solution (0.5 M) of N-methylpiperazine (1.2 mL, 0.60 mmol) was added to a THF solution (0.5 M) of cyclohexanecarboxaldehyde (1.0 mL, 0.50 mmol). MP-Triacetoxyborohydride (2.0 mmol/g, 0.625 g, 1.25 mmol) was then added and the mixture was agitated for 16 h at room temperature. When the reaction was complete, PS-Isocyanate (0.4 g, 0.5 mmol) and THF (2 mL) were added and the mixture was further agitated for 6 h. The solution was filtered and the resin was washed with THF (2×4 mL). The combined solution was concentrated to afford the tertiary amine product in 92% yield and 99% purity. The tertiary amine was characterized by gas chromatography and $^1$H NMR.

Discussion of Example

Reductive amination using secondary amines was carried out with carbonyl compounds as the limiting reagent. PS-Isocyanate (Argonaut Technologies) was added to the reaction mixture to selectively scavenge excess secondary amine. Tertiary amine product was isolated as a free amine by filtration and subsequent evaporation of the solvent. Reductive amination using secondary amines may also be carried out with amine as the limiting reagent to drive the reaction to completion. In these cases, the product amines may be purified from non-basic impurities by "catch and release" using MP-TsOH columns. The results for reductive amination using a set of secondary amines are summarized below in Table 2. The expected products were obtained for both cyclic secondary amines with aldehydes and ketones (entries 1-4, Table 2). Alicyclic secondary amines, e.g., N-benzylmethylamine underwent smooth transformation to the corresponding tertiary amines in high purity (entries 5 and 6, Table 2).

TABLE 2

Reductive Amination using Secondary Amines and MP-Triacetoxyborohydride

| Entry | Starting Amine | Carbonyl Compound | Product Amine | % Yield (isolated) | % Purity |
|---|---|---|---|---|---|
| 1 | | | | 92 | 99 |
| 2 | | | | 85 | 100 |
| 3 | | | | 63 | 100 |
| 4 | | | | 69 | 100 |
| 5 | | | | 82 | 100 |
| 6 | | | | 76 | 100 |

Example 4

Reductive Amination Using Amine Hydrochlorides

Scheme 5: Reductive Amination with Amine Hydrochlorides

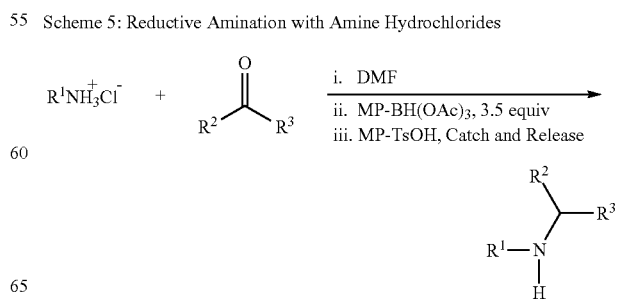

Representative Procedure for Reductive Amination Using Primary Amine Hydrochlorides Entry 3, Table 3

A DMF solution (0.25 M) of HCl-Tyr(OBn)-OMe (2 mL, 0.5 mmol) was added to a DMF solution (0.5 M) of cyclopentanone (1.2 mL, 0.60 mmol). MP-Triacetoxyborohydride (2.3 mmol/g, 0.760 g, 1.75 mmol) was then added and the mixture was agitated for 16 h at room temperature. The resin was filtered with a 6-mL fritted polypropylene cartridge into a scintillation vial containing MP-TsOH (1.0 g, 1.5 mmol). The MP-Triacetoxyborohydride resin was rinsed with DMF (3×2 mL) and the combined filtrate was agitated with MP-TsOH for 45 min. The mixture was transferred to a polypropylene cartridge fitted with a nylon stopcock to control the flow rate to approximately 0.5-1.5 mL/min. The MP-TsOH resin was washed with MeOH (4×8 mL) to remove non-basic impurities. The product was released by washing with 2 M $NH_3$/MeOH, and MeOH (2×8 mL). The combined solution was concentrated to afford the secondary amine product in 60% yield and 93% purity. The secondary amine was characterized by gas chromatography and $^1H$ NMR.

Discussion of Example

Reductive amination using hydrochloride salts of amino esters was carried out using DMF as the reaction solvent. The reaction was performed in the presence of 3.5 equiv of MP-Triacetoxyborohydride with amine as the limiting reagent. Isoleucine methyl ester hydrochloride underwent reductive alkylation with cyclopentanone and cyclohexanecarboxaldehyde, respectively, to afford the corresponding secondary amine products in high yield and purity (entries 1 and 2, Table 3). Notably, overalkylation was not observed even in the presence of excess carbonyl compound. Reductive amination using tyrosine methyl ester hydrochloride afforded analogous results (entries 3 and 4, Table 3). N-methylpyrrolidone was equally effective as the solvent for these reactions. Since carbonyl compounds were used in excess, the products were purified by "catch and release" using MP-TsOH. This method effected convenient DMF separation from the product by elution with MeOH prior to product release with ammonia/methanol.

TABLE 3

Reductive Amination using Amino Ester Hydrochlorides and MP-Triacetoxyborohydride in DMF

| Entry | Starting Amine | Carbonyl Compound | Product Amine | % Yield (isolated) | % Purity |
|---|---|---|---|---|---|
| 1 | isoleucine methyl ester·HCl | cyclopentanone | N-cyclopentyl isoleucine methyl ester | 59 | 98 |
| 2 | isoleucine methyl ester·HCl | cyclohexanecarboxaldehyde | N-(cyclohexylmethyl) isoleucine methyl ester | 93 | 99 |
| 3 | O-benzyl tyrosine methyl ester·HCl | cyclopentanone | N-cyclopentyl O-benzyl tyrosine methyl ester | 60 | 93 |
| 4 | O-benzyl tyrosine methyl ester·HCl | cyclohexanecarboxaldehyde | N-(cyclohexylmethyl) O-benzyl tyrosine methyl ester | 74 | 98 |

Example 5

Reduction of N-Benzylidineaniline

Scheme 6: Reduction of Imine

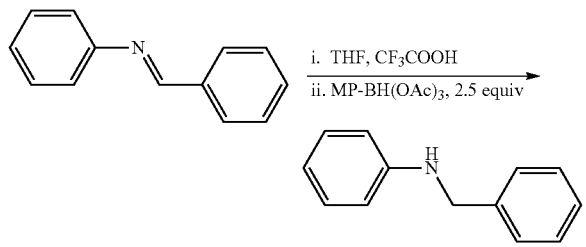

Representative Procedure for the Reduction of N-Benzylidineaniline:

To a solution of N-benzylidineaniline (0.09 g, 0.50 mmol) in THF (4.0 mL) was added trifluoroacetic acid (0.06 ml, 0.75 mmol). MP-Triacetoxyborohydride (2.0 mmol/g, 0.625 g, 1.25 mmol) was then added and the mixture was agitated for 6 h at room temperature. When the reaction was complete, the solution was filtered and the resin was washed with THF (2×4 mL). The combined solution was concentrated to afford the trifluoroacetate salt of N-benzylaniline in 94% yield and 99% purity. The amine was characterized by $^1$H NMR.

Ether Stabilization of Resins

The synthesis of many of the triacetoxyborohydride resins herein were performed in anhydrous THF as the selected solvent. If the THF is removed by vacuum drying at the end of the synthesis, which is considered a normal procedure to isolate the resins, the dried resins in most cases showed no activity immediately after drying, and those few batches that were initially active gradually lost all activity in approximately ten (10) days. In accordance with one aspect of the invention, resin samples herein may be prepared containing some amount of imbibed THF. These resins are found to be very stable and can maintain their activity.

THF was shown to stabilize the resins provided herein thus suppressing decomposition of the active functionality. This was exemplified by taking a freshly prepared lot of MP-Triacetoxyborohydride (sr200-87) (containing ~50% THF by weight) and drying a portion of this lot to 10 wt % THF and a second portion to complete dryness. The level of THF was confirmed both gravimetrically and by $^1$H-NMR of a chloroform-d extract. Measurement of the activity (by hydrogen out-gassing) showed that both samples had the same initial loading of 2.7 mmol/g. Over the course of 10 days at room temperature, the dry sample lost all activity. In contrast, a sample with 10 wt % THF maintained its loading above the theoretical loading for 30 days at room temperature (Graph 1). This was determined to be reproducible as indicated by the stability of sample sr200-89 which contained 10 wt % THF. This finding was unexpected since a similar effect is not observed for sodium triacetoxyborohydride or tetramethylammonium triacetoxyborohydride or other typical borohydride resins.

Generally ether solvents are known to form stable complexes with neutral boron hydrides, such as borane ($BH_3$), and other ionic metal hydrides, such as lithium aluminum hydrides (LAlH. The electron donating properties of the oxygen in THF may be responsible for the benefits recognized by this aspect of the invention. Other ether solvents may thus act similarly with resins provided herein including: ethyl ether, ethylene glycol dimethyl ether, ethylene glycol diethyl ether, diethylene glycol dimethyl ether, diethylene glycol diethyl ether, diethylene glycol dibutyl ether, triethylene glycol dimethyl ether, triethylene glycol diethyl ether, tetraethylene glycol dimethyl ether, tetraethylene glycol dimethyl ether, methyl end-capped oligoethylene glycol, methoxyethyl acetate, methoxypropanol acetate, diethylene glycol ethyl ether acetate, dioxane, tetrahydropyran, anisole, phenyl ether, and dibenzyl ether. In addition to ethereal solvents, other non-reacting organic solvents may also act similarly to stabilize the resins provided herein. These other solvents include but are not limited to the following: chlorinated solvents such as dichloroethane, chlorobenzene, fluorinated solvents such as fluorobenzene, and hydrocarbons such as toluene, xylene, hexanes, heptanes.

The ability to stabilize the bound triacetoxyborohydride functionality is an important and practical aspect of the resins formed in accordance with the invention. The shelf-life and ability to store these resins are critical benefits offered by this aspect of the invention which provide viable commercial products.

Resins herein may also hold some level of solvent without changing their physical characteristics, i.e., they still behave like dry beads in their handling rather than in a clump like a wet solid. In the case of MP-Triacetoxyborohydride, it was observed that beads were handled and flowed well in transfers with imbibed THF of up to about 25 wt % THF. At 30 wt % THF, the resin however tends to form clumps and may not transfer well. It is preferable that the resin is not clumped and flows well for dispensing in practical applications.

The amount of imbibed THF selected to stabilize the resins for the solid-supports herein is further observed to be relatively quite low.

Furthermore the functionality of these supported reagents may be kept for relatively extended periods of time. For example, a MP-Triacetoxyborohydride resin sample with 3% THF was shown to be stable after 6 months of storage at 4° C. (Table 4). After 5 months some of the sample was warmed to room temperature, and continued to show no decrease in activity, even when the THF level dropped to ca 1% (some loss in THF is experienced during storage and handling of resin due to evaporation).

TABLE 4

Stability Profile of MP-Triacetoxyborohydride

| Days stored | Storage Temp | % THF | Loading |
|---|---|---|---|
| 0 | 4° C. | 2.8 | 2.2 |
| 152 | 4° C. | 3.3 | 2.0 |
| 162 | 4° C. | 3.1 | 2.1 |
| 191 | 4° C. | 1.7 | 2.1 |
| 385 | 4° C. | 2.0 | 2.0 |
| 0 | ambient | 1.7 | 2.0 |
| 13 | ambient | 1.7 | 2.0 |
| 20 | ambient | 1.4 | 2.1 |
| 41 | ambient | 1.3 | 2.0 |

While the present invention is disclosed by reference to the preferable embodiments herein and the examples detailed above, it shall be understood that these examples are intended to be construed as illustrative rather than in a limiting sense. It is contemplated that any modifications and variations will readily occur to those skilled in the art, and that such modifications and variations are intended to fall within the scope of the present invention.

What is claimed is:

1. A modified solid-support for reduction reactions which comprises: a solid-support having a tetrasubstituted ammonium cation species ionically bonded to a borohydride anion species extending there from having the general formula:

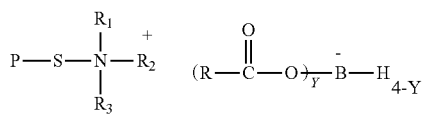

wherein
P is a solid-support, which is a macroporous polystyrene, and S is an alkylene spacer $R^1$, $R_2$, and $R_3$ are each ethyl, R is methyl, Y equals 3, H is hydrogen or deuterium; and
an organic solvent wherein said organic solvent is tetrahydrofuran (THF) and stabilizes said solid-supported reagent during storage.

2. A modified solid support according to claim 1 wherein the solid-supported reagent comprising the THF has a higher activity than a solid-supported reagent in which the solvent is removed.

3. A modified solid-support according to claim 1 wherein said tetrahydrofuran is from about 1.3 to 25 wt %.

4. A modified solid support according to claim 1 wherein the amount of said THF is about 1.3 wt % to about 30 wt %.

5. A modified solid support according to claim 1 wherein the amount of said THF is about 3 wt % to about 30 wt %.

6. A modified solid support according to claim 1 wherein the amount of said THF is about 10 wt %.

7. A modified solid support according to claim 1 wherein the amount of said THF is about 25 wt %.

8. A method for synthesizing a modified solid-support of claim 2 for use in solid phase synthesis comprising:
providing a solid-support of a macroporous methylpolystyrene having a triethylammonium borohydride group extending therefrom;
exposing the solid-support with a solution containing THF and acetic acid;
performing a substitution reaction whereby three of the hydrogen atoms bonded to the boron atom is exchanged for an acetate group; and
removing the solution until less than 30 wt % of the THF remains.

9. A modified solid support according to claim 1 wherein the solid-supported reagent comprising the THF has a higher activity at 6 days of storage than a solid-supported reagent in which the solvent is removed.

10. A modified solid support according to claim 1 wherein the solid-supported reagent comprising the THF has a higher activity at 30 days of storage than a solid-supported reagent in which the solvent is removed.

11. A modified solid support according to claim 1 wherein S is methylene.

12. A method of conducting an organic synthesis reduction reaction, which comprises reacting reagents for an organic synthesis reduction in the presence of the modified solid support of claim 2.

13. A method of reductively aminating a carbonyl group, which comprises reacting reagents for reductive amination of a carbonyl group in the presence of the modified solid support of claim 2.

14. A method of reductively alkylating an amino group, which comprises reacting reagents for reductive alkylation of an amino group in the presence of the modified solid support of claim 2.

* * * * *